US008869598B2

(12) United States Patent
Furman et al.

(10) Patent No.: US 8,869,598 B2
(45) Date of Patent: Oct. 28, 2014

(54) METHODS AND SYSTEMS FOR MONITORING A SEAL ASSEMBLY

(75) Inventors: Anthony Holmes Furman, Scotia, NY (US); John Saunders Stevenson, Yorba Linda, CA (US); Raymond Douglas Steele, Houston, TX (US); Beth Etta McCracken, Houston, TX (US)

(73) Assignee: General Electric Company, Schenectady, NY (US)

( * ) Notice: Subject to any disclaimer, the term of this patent is extended or adjusted under 35 U.S.C. 154(b) by 1098 days.

(21) Appl. No.: 12/854,738

(22) Filed: Aug. 11, 2010

(65) Prior Publication Data
US 2012/0036823 A1 Feb. 16, 2012

(51) Int. Cl.
*G01M 3/26* (2006.01)
*F23N 5/24* (2006.01)

(52) U.S. Cl.
CPC ............ *F23N 5/242* (2013.01); *F23N 2031/18* (2013.01); *Y02E 20/16* (2013.01); *Y02E 20/18* (2013.01)
USPC ........................................................ 73/40.7

(58) Field of Classification Search
USPC ................... 73/40.7, 46, 49.2, 49.3
See application file for complete search history.

(56) References Cited

U.S. PATENT DOCUMENTS

| 4,216,821 A * | 8/1980 | Robin ........................... 165/11.1 |
| 4,618,323 A | 10/1986 | Mansour |
| 4,685,404 A | 8/1987 | Sheppard et al. |
| 5,000,580 A | 3/1991 | Leininger et al. |
| 5,643,394 A | 7/1997 | Maydan et al. |
| 5,713,576 A | 2/1998 | Wasser et al. |
| 5,813,846 A | 9/1998 | Newby et al. |
| 5,823,122 A | 10/1998 | Chronowski et al. |
| 5,947,716 A | 9/1999 | Bellamy et al. |
| 6,053,632 A | 4/2000 | Leininger |
| 6,062,068 A * | 5/2000 | Bowling ......................... 73/40.7 |
| 6,609,905 B2 | 8/2003 | Eroglu et al. |
| 6,679,049 B2 | 1/2004 | Kline et al. |
| 6,807,804 B2 | 10/2004 | Kline et al. |
| 6,820,412 B2 | 11/2004 | Kline et al. |
| 2003/0056572 A1* | 3/2003 | Werner .......................... 73/40.7 |
| 2004/0067461 A1 | 4/2004 | Ranke et al. |
| 2004/0209127 A1* | 10/2004 | Wang et al. ..................... 429/13 |
| 2006/0147853 A1 | 7/2006 | Lipp et al. |
| 2006/0242907 A1 | 11/2006 | Sprouse et al. |
| 2009/0145200 A1* | 6/2009 | Kumar et al. ................... 73/40.7 |
| 2010/0170253 A1 | 7/2010 | Berry et al. |

OTHER PUBLICATIONS

FCCU Feed Injector Cold Flow Modeling 90EN194/91017, Texaco CE&P Engineering Division, 5 pages.
3 Stream Injector Cold Flow Modeling Results, ChevronTexaco, Feb. 12, 2004, 5 pages.
Duane Brooker, et al., Feed Injector Nozzle Scale-Up Testing: Bete Fog Nozzle Inc., Apr. 4-16, 1994, 73 pages.
National Aeronautics and Space Adminstration, Liquid Rocket Engine Injectors, NASA Space Vehicle Design Criteria (Chemical Propulsion), Mar. 1976, 131 pages, NASA SP-8089, National Technical Information Services, Springfield, Virginia.

* cited by examiner

*Primary Examiner* — Daniel S Larkin
(74) *Attorney, Agent, or Firm* — Armstrong Teasdale LLP (57) ABSTRACT

A method for monitoring functionality of a seal assembly within an injector feed assembly is described. The method includes providing a buffer fluid to the seal assembly, measuring at least one of a pressure and a flow rate of the buffer fluid, and determining a functionality of the seal assembly based at least partially on the at least one of a pressure and a flow rate of the buffer fluid.

7 Claims, 10 Drawing Sheets

METHODS AND SYSTEMS FOR MONITORING A SEAL ASSEMBLY

BACKGROUND OF THE INVENTION

The present invention relates generally to reaction chambers, such as a reaction chamber included in a gasification system used in an integrated gasification combined-cycle (IGCC) power generation plant, and more particularly, to methods and apparatus for monitoring the functionality of seals between two process fluids.

Most known IGCC plants include a gasification system that is integrated with at least one power-producing turbine system. For example, at least some known gasification systems convert a mixture of fuel, air or oxygen, steam, and/or $CO_2$ into a synthetic gas, or "syngas." The syngas is channeled to the combustor of a gas turbine engine, which powers an electrical generator that supplies electrical power to a power grid. Exhaust from at least some known gas turbine engines is supplied to a heat recovery steam generator (HRSG) that generates steam for driving a steam turbine. Power generated by the steam turbine also drives an electrical generator that provides electrical power to the power grid.

At least some known gasification systems include an injection system that supplies a gasification reactor with process fluids to facilitate at least one exothermic reaction. The injection system may include a plurality of concentric bayonets that, in combination, form a plurality of channels that each supply the gasification reactor with a process fluid. However, current bayonet designs, and more specifically bayonet tips used by such systems, may be limited because of assembly and/or maintenance concerns.

BRIEF DESCRIPTION OF THE INVENTION

In one aspect, a method for monitoring functionality of a seal assembly within an injector feed assembly is provided. The method includes providing a buffer fluid to the seal assembly, measuring at least one of a pressure or a flow rate of the buffer fluid, and determining a functionality of the seal assembly based at least partially on the at least one of a pressure or a flow rate of the buffer fluid.

In another aspect, a seal monitoring system for monitoring functionality of at least one seal assembly in an injector feed assembly is provided. The injector feed assembly includes a first section and a second section, the second section configured for coupling to the first section, wherein the first section and the second section each comprise at least one wall that defines at least one channel. The system includes a buffer fluid supply system for supplying buffer fluid to a seal assembly positioned between the first section and the second section. The system also includes a buffer fluid monitoring system configured to monitor at least one of a pressure of the buffer fluid or a flow rate of the buffer fluid supplied to the seal assembly and to determine a functionality of the seal assembly based at least partially on the at least one of the buffer fluid pressure or buffer fluid flow rate.

In yet another aspect, a power generation plant is provided. The power generation plant includes at least one carbonaceous reactant source, at least one oxygenated fluid reactant source, and at least one reactor. The at least one reactor includes at least one injection device coupled in flow communication with the at least one carbonaceous reactant source and the at least one oxygenated fluid reactant source. The at least one injection device includes an adapter and a tip section. The tip section is configured to be releasably coupled to the adapter, wherein the adapter and the tip section each include at least one wall that defines at least one channel. The at least one injection device also includes a buffer fluid pressure control and monitoring system configured to supply buffer fluid to at least one seal assembly positioned between the adapter and the tip section and to monitor a functionality of the at least one seal assembly.

DETAILED DESCRIPTION OF THE INVENTION

Figure 1:
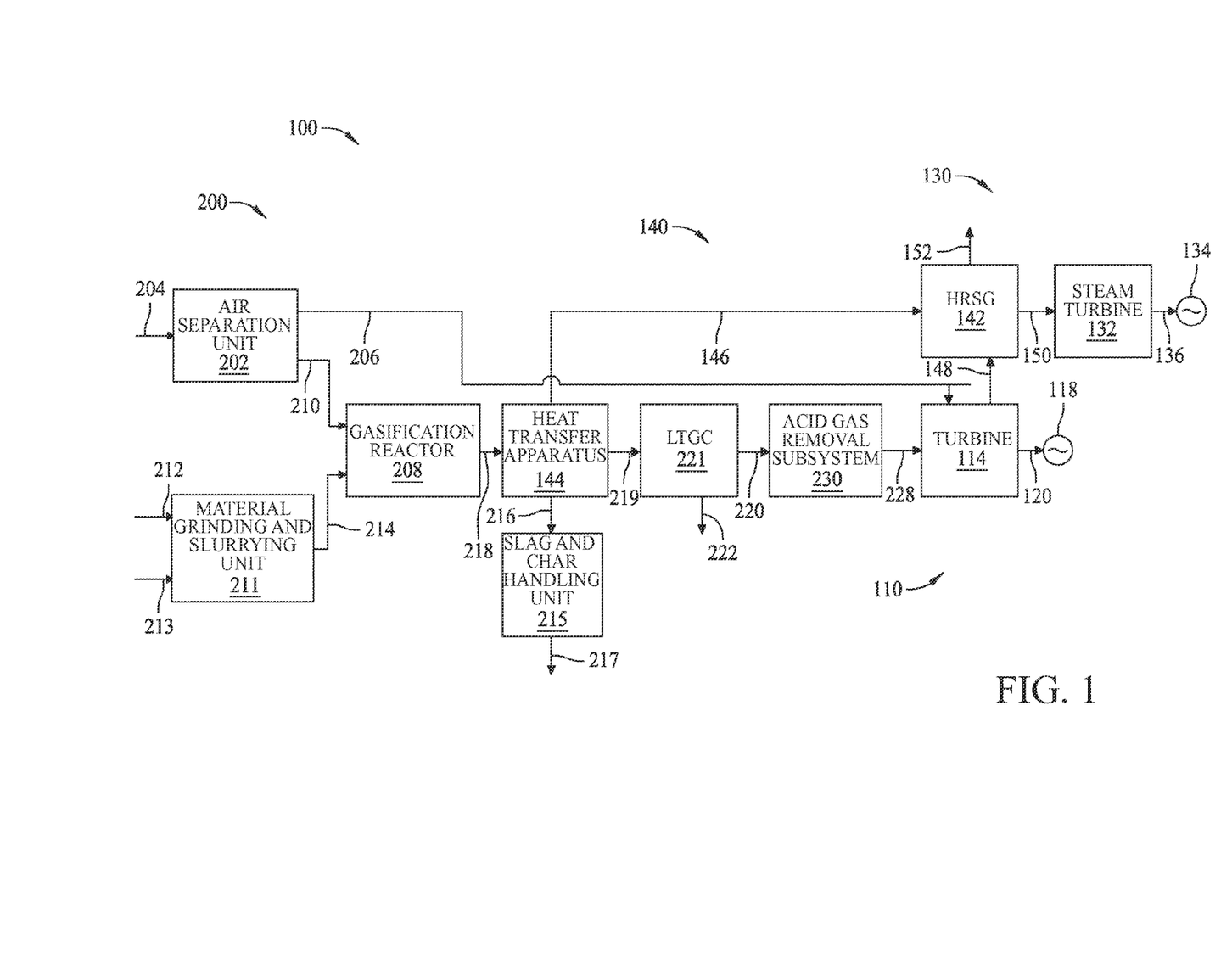
FIG. 1 is a schematic diagram of an exemplary integrated gasification combined-cycle (IGCC) power generation plant.

FIG. 1 is a schematic diagram of an exemplary gasification facility, specifically, an exemplary integrated gasification combined-cycle (IGCC) power generation plant 100. Alternatively, the method and apparatus to produce synthetic gas as described herein is used with any suitable gasification facility in any configuration that that enables such method and apparatus. In the exemplary embodiment, IGCC plant 100 includes a gas turbine engine 110. A turbine 114 is rotatably coupled to a first electrical generator 118 via a first rotor 120. Turbine 114 is coupled in flow communication with at least one fuel source and at least one air source (both described in more detail below) and is configured to receive the fuel and air from the fuel source and the air source (neither shown in FIG. 1), respectively. Turbine 114 mixes air and fuel, produces hot combustion gases (not shown), and converts the heat energy within the gases to rotational energy. The rotational energy is transmitted to generator 118 via rotor 120, wherein generator 118 converts the rotational energy to electrical energy (not shown) for transmission to at least one load, including, but not limited to, an electrical power grid (not shown).

IGCC plant 100 also includes a steam turbine engine 130. In the exemplary embodiment, engine 130 includes a steam turbine 132 rotatably coupled to a second electrical generator 134 via a second rotor 136.

IGCC plant 100 further includes a steam generation system 140. In the exemplary embodiment, system 140 includes at least one heat recovery steam generator (HRSG) 142 that receives exhaust gases (not shown) from turbine 114 via an exhaust gas conduit 148 that supplies heat used within HRSG 142 to produce one or more streams of steam from at least one boiler feedwater source that includes, but is not limited to, at least one heated boiler feedwater stream (not shown). HRSG 142 also is coupled in flow communication with at least one heat transfer apparatus 144 via at least one steam conduit 146. Apparatus 144 is also coupled in flow communication with at least one heated boiler feedwater conduit (not shown), wherein apparatus 144 receives heated boiler feedwater (not shown) from the same or a separate boiler feedwater source (not shown). HRSG 142 receives steam (not shown) from apparatus 144 via conduit 146, wherein HRSG 142 facilitates addition of heat energy to the steam. HRSG 142 is coupled in flow communication with turbine 132 via a steam conduit 150. In the exemplary embodiment, the cooled combustion gases are exhausted from HRSG 142 to the atmosphere via stack gas conduit 152. Alternatively, at least a portion of the excess combustion gases from HRSG 142 are channeled for use elsewhere in IGCC plant 100.

Conduit 150 is configured to channel steam (not shown) from HRSG 142 to turbine 132. Turbine 132 is configured to receive the steam from HRSG 142 and convert the thermal energy in the steam to rotational energy. The rotational energy is transmitted to generator 134 via rotor 136, wherein generator 134 is configured to facilitate converting the rotational energy to electrical energy (not shown) for transmission to at least one load, including, but not limited to, the electrical power grid. The steam is condensed and returned as boiler feedwater via a condensate conduit (not shown). Alternatively, at least a portion of the steam from HRSG 142, steam turbine 132 and/or heat transfer apparatus 144 is channeled for use elsewhere in IGCC plant 100.

IGCC plant 100 also includes a gasification system 200. In the exemplary embodiment, system 200 includes at least one air separation unit 202 coupled in flow communication with an air source via an air conduit 204. The air sources include, but are not limited to, dedicated air compressors (not shown) and a compressor (not shown) typically associated with gas turbine engine 110. Unit 202 is configured to separate air into one or more streams of oxygen ($O_2$), nitrogen ($N_2$), and other component streams (neither shown). The other component streams may be released via a vent (not shown) or collected in a storage unit (not shown). In the exemplary embodiment, at least a portion of $N_2$ is channeled to gas turbine 114 via an $N_2$ conduit to facilitate combustion.

System 200 includes a gasification reactor 208 that is coupled in flow communication with unit 202 and is configured to receive the $O_2$ channeled from unit 202 via an $O_2$ conduit 210. System 200 also includes a material grinding and slurrying unit 211. Unit 211 is coupled in flow communication with a carbonaceous material source and a water source (neither shown) via a carbonaceous material supply conduit 212 and a water supply conduit 213, respectively. In the exemplary embodiment, the carbonaceous material is petroleum coke, or pet coke. Moreover, in the exemplary embodiment, unit 211 is configured to mix the pet coke and water to form a pet coke slurry stream (not shown) that is channeled to reactor 208 via a pet coke slurry conduit 214. Alternatively, any suitable material that includes carbonaceous solids is used that facilitates operation of IGCC plant 100 as described herein. Also, alternatively, non-slurry fuels that include solid, liquid, and/or gaseous fuel substances are used, including mixtures of fuels and other materials, such as but not limited to, fuel and slag additives.

Reactor 208 is configured to receive the material slurry stream and an $O_2$ stream via conduits 214 and 210, respectively. Reactor 208 is also configured to facilitate production of a hot, raw synthetic gas (syngas) stream (not shown). Moreover, reactor 208 is also configured to produce hot slag and char (both not shown) as a by-product of the syngas production.

Reactor 208 is coupled in flow communication with heat transfer apparatus 144 via a hot syngas conduit 218. Apparatus 144 is configured to receive the hot, raw syngas stream and transfer at least a portion of the heat to HRSG 142 via conduit 146. Subsequently, apparatus 144 produces a cooled, raw syngas stream (not shown) that is channeled to a scrubber and low temperature gas cooling (LTGC) unit 221 via a syngas conduit 219. Unit 221 is configured to remove the portion of slag and char entrained within the raw syngas stream (sometimes referred to as "fines") and facilitate removal of the fines via a fines conduit 222. The fines are sent to a waste collection system (not shown) for ultimate disposal and/or recirculated back into gasification reactor 208 to take advantage of unused carbon content within the fines. Unit 221 is also configured to further cool the raw syngas stream.

Apparatus 144 also facilitates removal of slag and char from the hot, raw syngas stream. Specifically, a slag and char handling unit 215 is coupled in flow communication with apparatus 144 via a hot slag conduit 216. Unit 215 is configured to quench the balance of the char and slag, simultaneously breaking up the slag into small pieces wherein a slag and char removal stream (not shown) is produced and channeled through conduit 217. In a manner similar to the fines discussed above, the slag and char are channeled to a waste collection subsystem (not shown) for ultimate disposal and/or recirculated back into gasification reactor 208 to take advantage of unused carbon within the slag and char.

System 200 further includes an acid gas removal subsystem 230 that is coupled in flow communication with unit 221 and is configured to receive the cooled raw syngas stream via a raw syngas conduit 220. Subsystem 230 is also configured to facilitate removal of at least a portion of acid components (not shown) from the raw syngas stream as discussed further below. Such acid gas components include, but are not limited to, $H_2S$ and $CO_2$. Subsystem 230 is further configured to facilitate separation of at least some of the acid gas components into components that include, but are not limited to, $H_2S$ and $CO_2$. In the exemplary embodiment, $CO_2$ is not recycled and/or sequestered. Alternatively, subsystem 230 is coupled in flow communication with reactor 208 via at least one $CO_2$ conduit (not shown) wherein a stream of $CO_2$ (not shown) is channeled to predetermined portions of reactor 208. The removal of such $CO_2$ and $H_2S$ via subsystem 230 facilitates producing a clean syngas stream (not shown) that is channeled to gas turbine 114 via a clean syngas conduit 228.

In operation, air separation unit 202 receives air via conduit 204. The air is separated into $O_2$, $N_2$, and other components. The other components are vented or collected, wherein at least a portion of $N_2$ is channeled to turbine 114 via a conduit 206 and at least a portion of $O_2$ is channeled to gasification reactor 208 via conduit 210. Remaining portions of $N_2$ and $O_2$ may be channeled as a plurality of streams to other portions of IGCC plant 100 as needed, including, but not limited to, storage. Also, in operation, material grinding and slurrying unit 211 receives pet coke and water via conduits 212 and 213, respectively, forms a pet coke slurry stream and channels the pet coke slurry stream to reactor 208 via conduit 214.

Reactor 208 receives the $O_2$ via conduit 210, pet coke via conduit 214. Reactor 208 facilitates production of a hot raw syngas stream that is channeled to apparatus 144 via conduit 218. Some of the slag by-product that is formed in reactor 208 is removed via slag handling unit 215 and conduits 216 and 217. Apparatus 144 facilitates cooling the hot raw syngas stream to produce a cooled raw syngas stream that is channeled to scrubber and LTGC unit 221 via conduit 219 and the syngas is cooled further. Particulate matter, including some of the slag and char (in the form of fines), is removed from the syngas via conduit 222. The cool raw syngas stream is channeled to acid gas removal subsystem 230 wherein acid gas components are selectively removed such that a clean syngas stream is formed and channeled to gas turbine 114 via conduit 228.

Further, in operation, turbine 114 receives $N_2$ and clean syngas via conduits 206 and 228, respectively. Turbine 114 compresses air from at least one air source (not shown) that turbine 114 subsequently mixes and combusts with the syngas fuel, producing hot combustion gases. Turbine 114 channels the hot combustion gases to induce rotation of turbine 114 which subsequently rotates first generator 118 via rotor 120. At least a portion of the exhaust gases are channeled to HRSG 142 from turbine 114 via an exhaust gas conduit 148 to facilitate generating steam.

At least a portion of the heat removed from the hot syngas via heat transfer apparatus 144 is channeled to HRSG 142 as steam via conduit 146. HRSG 142 receives the steam from apparatus 144, together with one or more streams of boiler feed water, as well as the exhaust gases from turbine 114. Heat is transferred from the exhaust gases to the one or more streams of boiler feedwater as well as the steam from apparatus 144, thereby producing one or more subsequent streams of steam as well as increasing the heat energy contained in the steam from apparatus 144. In the exemplary embodiment, at least one of the streams of steam generated as described above is heated to superheated conditions. Alternatively, one or more of the aforementioned streams of steam are mixed together to form one or more mixed streams that may be heated to superheated conditions. Alternatively, high temperature saturated steam is formed. At least a portion of the superheated steam is channeled to steam turbine 132 via conduit 150 and induces a rotation of turbine 132. Turbine 132 rotates second generator 134 via second rotor 136. A remaining portion of the steam is channeled for use elsewhere within IGCC plant 100.

Figure 2:
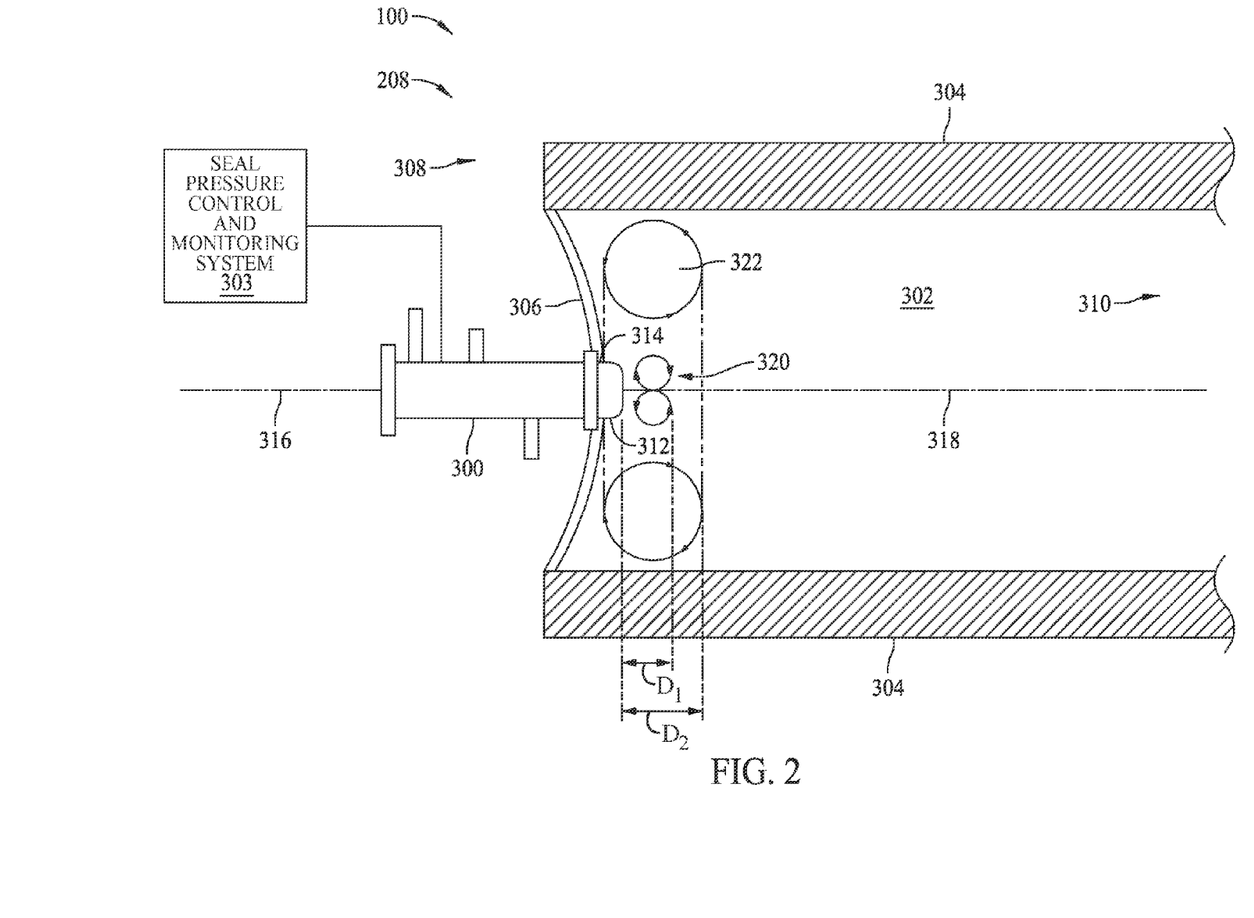
FIG. 2 is a schematic cross-sectional view of a gasification reactor that may be used for synthetic gas generation, such as may be used with the IGCC power generation plant shown in FIG. 1.

FIG. 2 is a schematic cross-sectional view of gasification reactor 208 that may be used for synthetic gas generation, such as may be used with IGCC power generation plant 100. Reactor 208 includes at least one injection device 300 (also referred to herein as injector 300) that is coupled in flow communication with a gasification cavity 302. In the exemplary embodiment, device 300 is an annular triplet gasifier injector nozzle as described herein, thereby including three annular passages (described further below). Alternatively, device 300 is any suitable injector nozzle that includes, but is not limited to, configurations with four or more annular passages. Further, alternatively, device 300 is any suitable injector nozzle that includes, but is not limited to, three or more concentric passages, wherein each passage is coupled in flow communication with the annular passages described above in any configuration that facilitates operation of injection device 300 as described herein. Furthermore, in the exemplary embodiment, a seal pressure control and monitoring system 303 is in communication with injection device 300.

Cavity 302 is at least partially defined by a substantially cylindrical reactor wall 304 and a head end cover 306. In the exemplary embodiment, gasification reactor 208 is substantially cylindrical. Alternatively, reactor 208 includes any configuration that facilitates operation of reactor 208 as described herein. Also, in the exemplary embodiment, device 300 has a substantially vertical orientation (described further below) wherein device 300 penetrates the top of reactor 208 and points substantially downward. Alternatively, device 300 has any orientation including, but not limited to, substantially horizontal orientations.

In the exemplary embodiment, wall 304 includes at least one ceramic refractory material that includes, but is not limited to, heat tempered bricks. Alternatively, wall 304 is fluid-cooled, wherein the cooling fluids include, but are not limited to, nitrogen, water, and/or steam. Cover 306 is sealingly coupled to at least a portion of a head end portion 308 of reactor 208. Cavity 302 is also partially defined by a tail end cover (not shown) that is sealingly coupled to at least a portion of wall 304, wherein the tail end cover is positioned on a tail end portion 310 that is in opposition to portion 308. Alternatively, cover 306, head end portion 308, the tail end cover and tail end portion 310 are oriented in any position relative to wall 304, including any orientation that facilitates operation of reactor 208 as described herein. Furthermore, wall 304 may be of any configuration that facilitates operation of reactor 208 as described herein. Moreover, alternatively, reactor 208 has any suitable configuration that facilitates operation of IGCC plant 100 as described herein.

Injection device 300 includes a tip portion 312 that is inserted through an aperture 314 defined in head end cover 306 and sealingly coupled to head end cover 306 using a fastening method that includes, but is not limited to, retention hardware (not shown in FIG. 2). Reactor 208 is configured such that an axial centerline 316 of injection device 300 is collinear with a longitudinal centerline 318 of gasification cavity 302. Tip portion 312 is configured to form a plurality of recirculation zones within cavity 302. Specifically, tip portion 312 is configured to form a first recirculation zone 320 a first distance $D_1$ from tip portion 312 within gasification cavity 302. Recirculation zone 320 has a shape that is substantially toroidal and the shape is one of substantially spatially continuous or partially segmented. Moreover, recirculation zone 320 is positioned close to and, with respect to centerline 318, substantially centered about centerline 318. Also, specifically, tip portion 312 is configured to form a second recirculation zone 322 a second distance $D_2$ from tip portion 312 within gasification cavity 302. Recirculation zone 322 has a shape that is substantially toroidal and the shape is one of substantially spatially continuous or partially segmented. Moreover, recirculation zone 322 is positioned with respect centerline 318, that is, substantially centered about centerline 318, and in close proximity to wall 304. First recirculation zone 320 is proximately centered within second recirculation zone 322.

Alternative embodiments of reactor 208 may include a plurality of injection devices 300, wherein each device 300 has a centerline 316, such that each associated centerline 316 is co-linear with a predefined axial orientation similar to centerline 318. Each of such plurality of devices 300 may have either a vertical, i.e., directly upward and/or directly downward, and/or a horizontal orientation, including any orientation between purely vertical and purely horizontal orientations, that facilitates operation of reactor 208 as described herein. Furthermore, such alternative embodiments of reactor 208 may include a plurality of devices 300, wherein all of devices 300 have a substantially similar orientation. Moreover, such alternative embodiments of reactor 208 may include a plurality of devices 300, wherein a first number of such injectors 300 have a differing orientation than a second number of such devices 300.

Still further alternative embodiments of reactor 208 may include a plurality of devices 300 wherein devices 300 are distributed across one or more surfaces of reactor 208, each device 300 with a differing orientation, and in communication with system 303. Moreover, injectors 300 making up at least a portion of plurality of injectors 300 may each be placed in a dedicated cavity (not shown) that is a part of, or otherwise joined with, reactor 208, thereby facilitating separate formation or development of multiple recirculation zones from each such injector 300.

Figure 3:
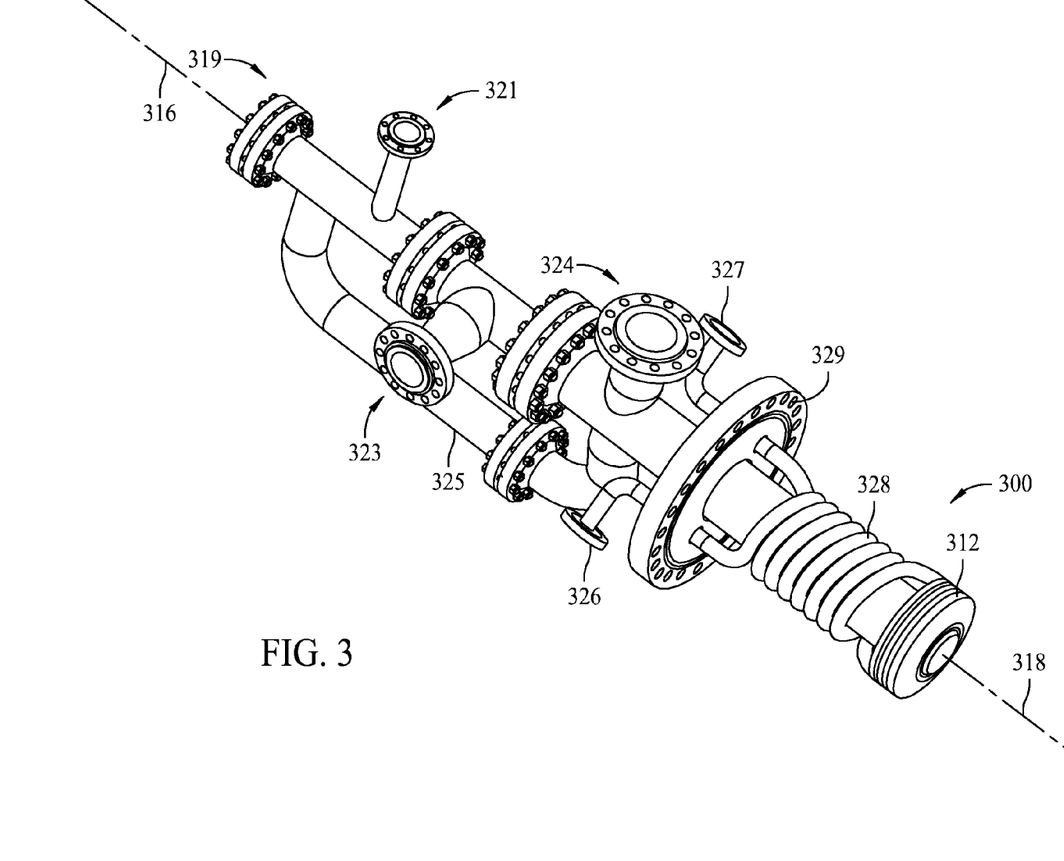
FIG. 3 is a schematic perspective view of an exemplary injector feed assembly that may be used with the gasification reactor shown in FIG. 2.

FIG. 3 is a schematic perspective view of an exemplary injector feed assembly 319 that may be used with gasification reactor 208 (shown in FIG. 2). Injection device axial centerline 316 and gasification cavity longitudinal centerline 318 are illustrated for perspective. Assembly 319 includes an inner oxygen ($O_2$) supply section 321 that is coupled in flow communication to an $O_2$ source similar to $O_2$ conduit 210 (shown in FIG. 1). Assembly 319 also includes a middle slurry section 323 that is coupled in flow communication to a slurry source similar to material slurry conduit 214 (shown in FIG. 1). Assembly 319 further includes an outer $O_2$ supply section 324 that is coupled in flow communication to an $O_2$ source similar to $O_2$ conduit 210. At least a portion of section 324 extends about at least a portion of section 323, at least a portion of section 323 extends about at least a portion of section 321, and, at least a portion of section 324 extends about at least a portion of section 321. Moreover, sections 321, 323, and 324 terminate where they join tip 312 in flow communication. Therefore, sections 321, 323 and 324 define a plurality of substantially concentric passages or channels, or, specifically, an inner $O_2$ channel, a middle slurry channel, and an outer $O_2$ channel (neither shown in FIG. 3) within assembly 319.

Assembly 319 also includes an $O_2$ bypass line 325 that establishes at least some flow communication between sections 324 and 321 such that a predetermined $O_2$ mass flow rate distribution is facilitated based at least partially upon cumulative predetermined $O_2$ pressure drops that occur as $O_2$ is channeled through sections 321 and 324, $O_2$ bypass line 325, and subsequent components as $O_2$ is discharged from assembly 319. Therefore, maintaining predetermined ratios of an outer $O_2$ mass flow rate and an inner $O_2$ mass flow rate (neither shown) are facilitated. Bypass line 325 facilitates installation and operation of assembly 319 in retrofits of gasification reactor 208. Alternatively, methods that include, but are not limited to flow orifices and manually-operated and automated throttle valves are used in conjunction with, or in lieu of, bypass line 325.

Assembly 319 further includes a cooling fluid inlet manifold 326 and a cooling fluid outlet manifold 327 coupled in flow communication with tip portion 312 of injection device 300 via a plurality of cooling fluid coils 328. Manifolds 326 and 327 and coils 328 facilitate channeling a cooling fluid to remove heat from tip portion 312 (discussed in more detail below). Assembly 319 also includes a mounting flange 329 that is removably and sealingly coupled to head end cover 306 using a fastening method that includes, but is not limited to, retention hardware (not shown). Alternatively, assembly 319 has any number of coolant connections and/or coolant flow means that facilitate operation of injection device 300 as described herein.

Figure 4:
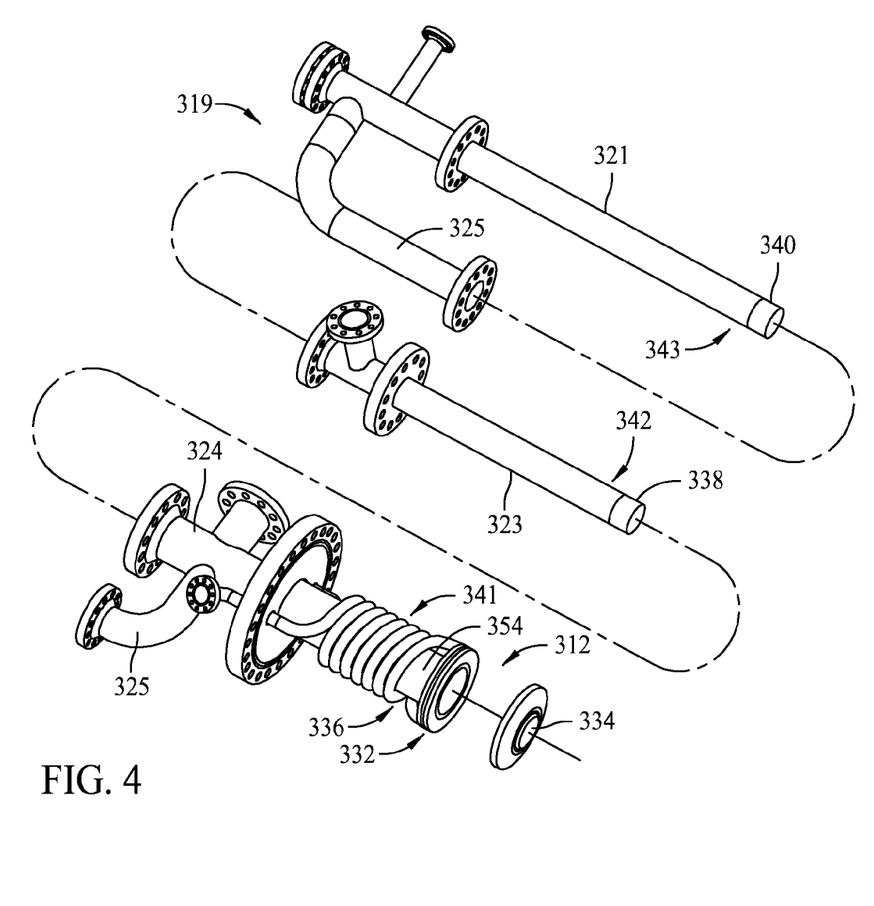
FIG. 4 is an exploded view of the exemplary injector feed assembly shown in FIG. 3.

FIG. 4 is an exploded view of the exemplary injector feed assembly 319. In the exemplary embodiment, inner oxygen supply section 321 is positioned at least partially within slurry supply section 323, which is at least partially positioned within outer oxygen supply section 324. Assembly 319 has a "bayonet" design, wherein sections 321, 323, and 324 herein are also referred to as bayonets and/or bayonet sections 321, 323, and 324. Bayonet section 321 includes an end 343, bayonet section 323 includes an end 342, and bayonet section 321 includes an end 341.

Figure 5:
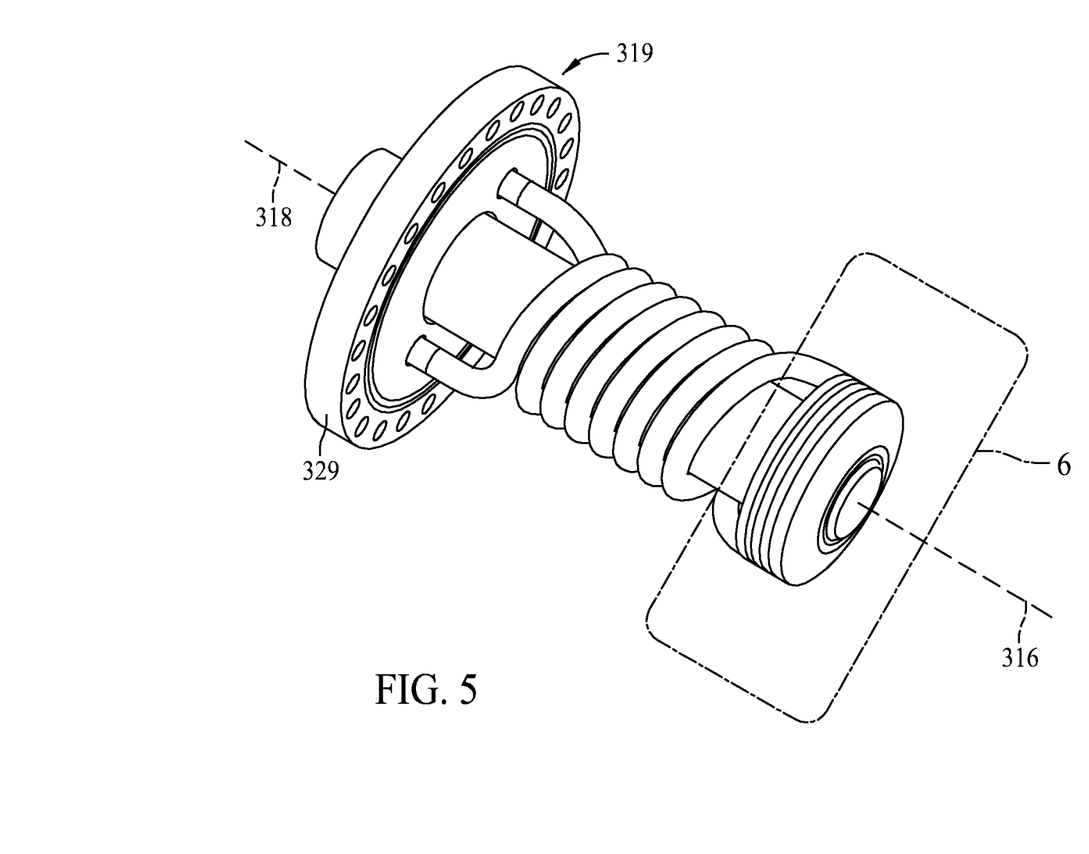
FIG. 5 is a schematic perspective view of a portion of the exemplary injector feed assembly shown in FIG. 3.
Figure 6:
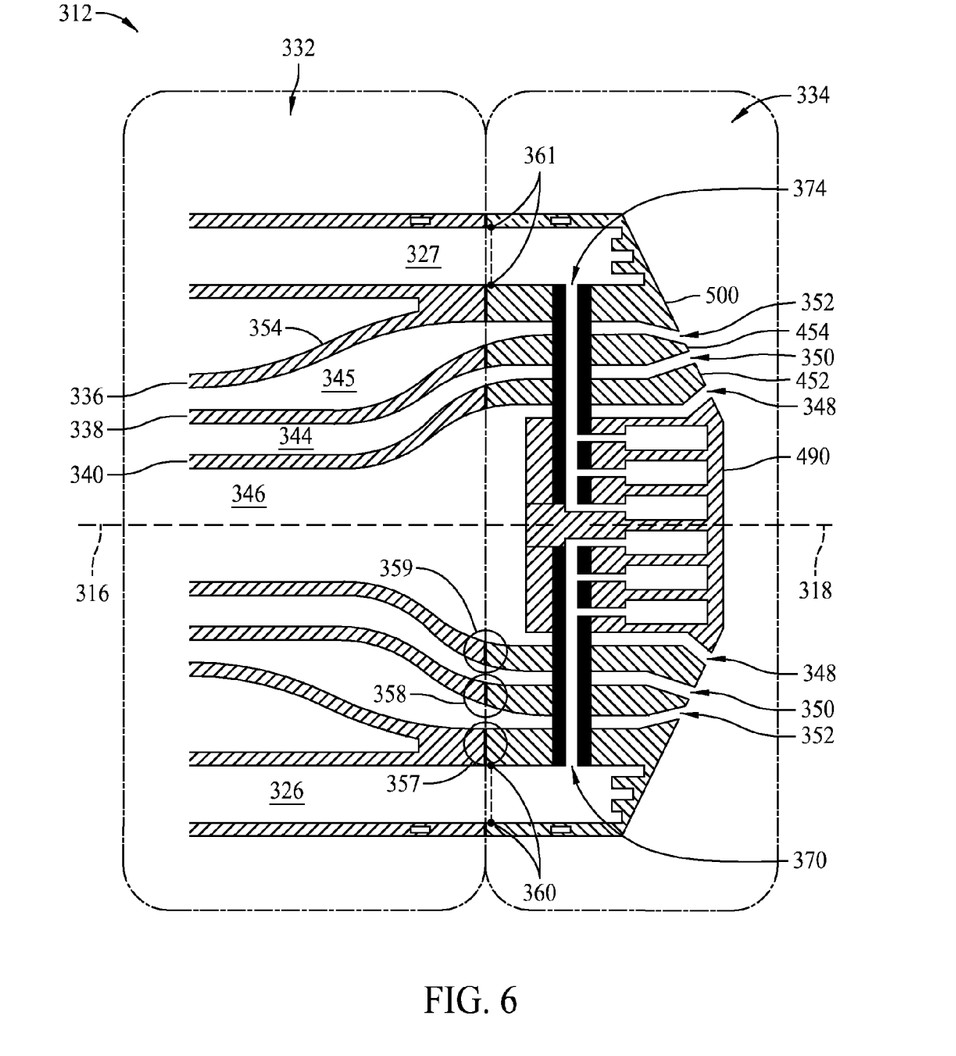
FIG. 6 is a schematic cross-sectional view of a tip portion of an injector feed assembly that may be used with the injector feed assembly of FIG. 5 taken along area 6.
Figure 7:
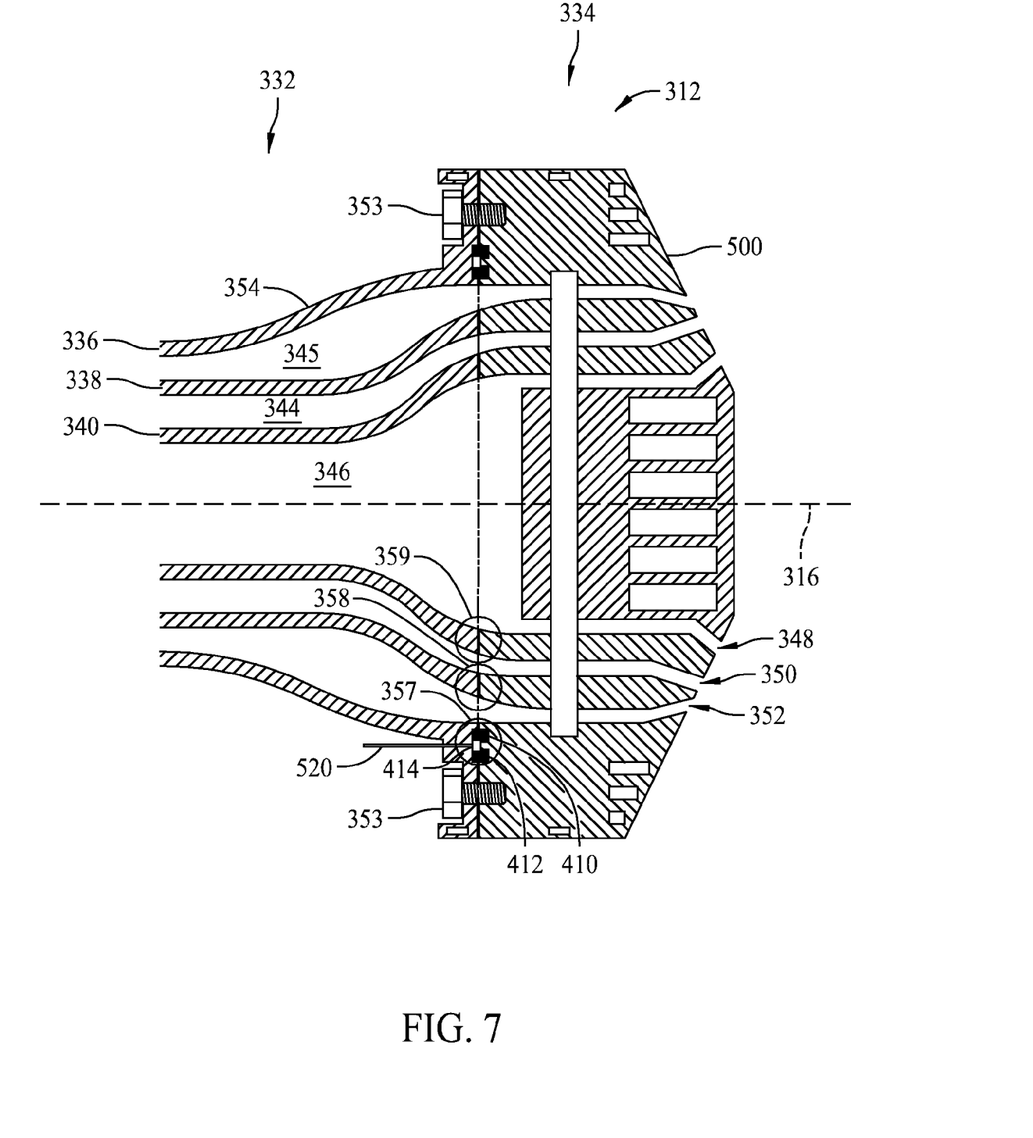
FIG. 7 is another schematic cross-sectional view of the exemplary tip portion shown in FIG. 5.

FIG. 5 is a schematic perspective view of a portion of injector feed assembly 319, including an area 6. FIG. 6 is a schematic cross-sectional view of tip portion 312 of injector feed assembly 319 taken along area 6 (shown in FIG. 5). Tip portion 312 controls the distribution of flow of reactant supply fluids between injector feed assembly 319 and gasification cavity 302 (shown in FIG. 2). FIG. 7 is another schematic cross-sectional view of the exemplary tip portion 312 shown in FIG. 5.

Moreover, as illustrated in the exemplary embodiment, adapter portion 332 includes three substantially annular adapters: an outer gaseous oxygen (GOX) bayonet adapter 336, a slurry bayonet adapter 338, and an inner GOX bayonet adapter 340. Bayonet adapters 336, 338, and 340 are coupled in flow communication with bayonet sections 324, 323 and 321 (all shown in FIG. 3), respectively. More specifically, outer GOX bayonet adapter 336 is coupled to an end 341 of bayonet section 324 (both shown in FIG. 4). Slurry bayonet adapter 338 is coupled to an end 342 of bayonet section 323 (both shown in FIG. 4). Inner GOX bayonet adapter 340 is coupled to an end 343 of bayonet section 321 (both shown in FIG. 4). Adapter portion 332 is coupled to injector feed assembly 319 via known methods such as, but not limited to, welding, brazing, and/or retention hardware (not shown).

In the exemplary embodiment, adapter portion 332 may be fabricated as a plurality of extensions of bayonet sections 321, 323, and 324 of assembly 319, rather than as a component or components of tip portion 312. That is, in the exemplary embodiment, outer GOX bayonet adapter 336, slurry bayonet adapter 338, and inner GOX bayonet adapter 340 are separate pieces that are individually coupled to bayonet sections 321, 323, and 324, respectively, during assembly of injector feed assembly 319. Alternatively, at least two of bayonet adapters 336, 338, and 340 are coupled together to form a single piece. That is, alternatively, tip portion 312 includes an integrated, unitarily-formed bayonet adapter portion 332 and a modular tip 334, wherein adaptor portion 332 is coupled to bayonet sections 321, 323, and 324 of assembly 319.

In the exemplary embodiment, slurry bayonet adapter 338 and inner GOX bayonet adapter 340 partially define a reactant, or slurry, channel 344. Slurry channel 344 is in flow communication with a middle coal slurry channel (not shown) defined and extending within assembly 319 (shown in FIG. 3). In the exemplary embodiment, slurry bayonet adapter 338 and outer GOX bayonet adapter 336 partially define an outer reactant channel, that is, an outer GOX channel 345, and inner GOX bayonet adaptor 340 partially defines an inner reactant channel, that is, an inner GOX channel 346. Inner GOX channel 346 and outer GOX channel 345 are coupled in flow communication with an inner and an outer oxygen channel (neither shown) defined and extending within assembly 319. Alternatively, either of channels 345 and 346 are oriented to channel any process fluid that facilitates operation of gasification reactor 208 including, but not limited to, steam, nitrogen and carbon dioxide, and channels 345 and 346 are coupled in flow communication with the appropriate fluid sources.

To form the first recirculation zone 320 and the second recirculation zone 322 (both shown in FIG. 2), tip portion 312 includes both diverging and converging nozzles. More specifically, a plurality of nozzles are formed within modular tip 334 including an inner GOX nozzle 348, a slurry nozzle 350, and an outer GOX nozzle 352. Inner GOX nozzle 348 and slurry nozzle 350 direct respective process fluids away from injector axial centerline 316, and are referred to as diverging nozzles. Outer GOX nozzle 352 directs a respective process fluid toward injector axial centerline 316, and is therefore referred to as a converging nozzle. Alternatively, outer GOX nozzle 352 is either a divergent nozzle or a parallel nozzle with respect to injector axial centerline 316.

Injection device 300, that includes injector feed assembly 319 with tip portion 312 having both diverging and converging nozzles including nozzles 348, 350, and 352, facilitates mixing of the reactant streams, that is, the slurry and GOX streams (neither shown) at predetermined angles with predetermined momentums. Nozzles 348, 350, and 352 also facilitate improving an efficiency of chemical reactions between the slurry and oxygen.

Orienting and configuring nozzles 348, 350, and 352 as discussed herein has beneficial results that include, but are not limited to, facilitating vaporization of the reactants. Specifically, forming recirculation zones 320 and 322 facilitates increasing a residence time of the slurry and GOX such that exothermic reactions between the carbonaceous material and GOX occur more effectively. Moreover, an additional benefit of forming such recirculation zones 320 and 322 in the vicinity of head end portion 308 (shown in FIG. 2) facilitates increasing heat release in that vicinity, and therefore facilitates vaporization of water in the slurry stream. However, due to localized exothermic reactions and associated heat releases, portions of injection device 300, that is, at least one outer surface of injection device 300, is exposed to hot syngas (not shown) including, but not limited to, external surface 354 (also shown in FIG. 4). Such high temperature exposures are discussed further below.

In general, initial assembly of, as well as post-commissioning field service and maintenance disassembly and reassembly of known injector assemblies are each complicated by including both diverging and converging nozzles within such injector assemblies. For example, in most cases, it is difficult to remove a known bayonet having a diverging tip that at least partially forms a diverging nozzle from a next larger known bayonet if the larger bayonet has a converging tip with a converging nozzle that is similar to, or smaller in size than the diverging tip, since such converging tip may interfere with axial removal of such diverging tip. Therefore, partial disassembly of tip portion 312 by disassembly of diverging nozzles 348 and 350 from converging nozzle 352 may be especially difficult. One method of disassembly where such interferences occur between the nozzles in the injector includes removing the injector (that is, injector 300 as described herein) from the reactor cavity (that is, cavity 302 as described herein and shown in FIG. 2), and cutting off the tips of the known bayonets.

However, in the exemplary embodiment, modular tip 334 simplifies assembly, disassembly, and field service of injection device 300 while facilitating the use of a combination of diverging and converging nozzles 348, 350, and 352. This simplification is achieved since the converging and diverging nozzles 348, 350, and 352 are formed within modular tip 334, which is releasably coupled to adapter portion 332. Bayonet adapters 336, 338, and 340 are sized such that each adapter and respective bayonet can be removed from the next larger adapter and respective bayonet when modular tip 334 is not coupled to adapter portion 332.

In the exemplary embodiment, modular tip 334 is fabricated as a single component from a plurality of individual components that are joined together by known coupling methods including, for example, brazing or welding. Alternatively, one-piece modular tip 334 may be formed by methods that include direct metal laser sintering. One-piece modular tip 334 is coupled in flow communication with adapter portion 332. Modular tip 334 may be fabricated as one-piece to achieve a desired degree of nozzle precision and also to ease field assembly and disassembly. Also, in the exemplary embodiment, modular tip 334 is removably coupled to adapter portion 332 via known coupling methods that include, but are not limited to, retention hardware 353 (discussed further below). Alternatively, modular tip 334 is removably coupled to adapter portion 332 via any known coupling methods that enable operation of modular tip 334 as described herein. Retention hardware 353 and external surface 354 are proximate to each other.

Further, in the exemplary embodiment, tip portion 312, which includes modular tip 334 and adaptor portion 332 removably coupled together via retention hardware 353 rather than welded together, also includes a plurality of seals that are used to maintain separation between slurry channel 344, outer GOX channel 345, inner GOX channel 346, cooling water manifold 326, cooling water manifold 327, and a flow of hot syngas (not shown) within cavity 302 that is external to injector feed assembly 319. More specifically, in the exemplary embodiment, a seal assembly 357 maintains a separation between outer GOX channel 345 and the syngas contacting external surface 354. Moreover, a seal assembly 358 maintains a separation between outer GOX channel 345 and slurry channel 344. In addition, a seal assembly 359 maintains a separation between slurry channel 344 and inner GOX channel 346. Furthermore, a seal assembly 360 facilitates maintaining a separation between cooling fluid inlet manifold 326, outer GOX channel 345, and hot syngas that contacts external surface 354. Still further, a seal assembly 361 facilitates maintaining separation between cooling fluid outlet manifold 327, outer GOX channel 345, and hot syngas that contacts external surface 354. Seal assemblies 357, 358, 359, 360, and 361 are manufactured from any materials in any configuration that enables operation of modular tip 334 as described herein including, without limitation, metallic seals, and o-rings, singular or redundant seals, and any combination thereof.

Each of seal assemblies 357, 358, 359, 360, and 361 facilitates preventing unintended mixing of the process fluids and coolants used in the gasification process while utilizing an injector tip that includes multiple components that are not connected together by welding or brazing.

In the exemplary embodiment, seal assembly 357 includes a plurality of seals, for example, seals 410 and 412, and at least one pressure port 414. The at least one pressure port 414 extends through GOX bayonet adapter 336 from the external surface 354 into seal assembly 357. The at least one pressure port 414 provides flow communication between seal pressure control and monitoring system 303 (shown in FIG. 2) and seals 410 and 412.

In the exemplary embodiment, seals 410 and 412 are high pressure fluid buffer seals that include, but are not limited to, two seals injected with a fluid, such as, nitrogen. An effectiveness, also referred to herein as the functionality, of the seals, such as whether a seal is leaking more than an amount predetermined to be acceptable, can be determined by monitoring the pressure of the nitrogen, the flow rate of the nitrogen, and/or a composition of a fluid, for example, process fluids being separated by the seal and/or the buffer fluid. Also, by injecting the nitrogen at a higher pressure than the pressure of the process fluids being separated, the nitrogen will be the first fluid to leak. Controlling which fluid initially leaks may prevent a potentially dangerous combination of fluids from accidentally mixing should a leak occur. For example, a dangerous combination of fluids, such as GOX and syngas, may severely damage injection device 300, gasification reactor 208, and other components within IGCC plant 100. However, if the nitrogen leaks out of the seal and the leak is detected, an orderly shutdown of gasification reactor 208 may be performed before the leak becomes worse, and any potentially dangerous fluids are mixed. The amount of time provided to perform the orderly shutdown while the higher pressure buffer fluid leaks out of the seal is at least partially dependent upon the severity of the leak, and the amount of buffer fluid that is available for injection into the seals.

Alternatively, a high pressure fluid buffer seal may also be used between inner GOX bayonet adapter 340 and inner GOX tip 452, and between slurry bayonet adapter 338 and slurry tip 454, as well as, or in place of, seal assemblies 360 and 361. For example, to prevent fluid from leaking between outer GOX bayonet adapter 336 and outer GOX tip 500, high pressure fluid buffer seals could replace or supplement seal assembly 360. The high pressure fluid buffer seals may be injected with a variety of fluids, as described above. For example, where nitrogen is used as a cooling fluid, a seal buffer gas of a different composition may be advantageous. For example, if argon is used as the seal buffer fluid, using argon in the seals would allow a leak to be detected by monitoring the composition of the cooling fluid. A detection of argon in the cooling fluid exceeding a predetermined level would indicate that a buffer seal leak has occurred. Although described with respect to seal assembly 360, a fluid buffer seal may be used in place of any seal or seal assembly described herein, and furthermore, may be used to prevent fluid leaks between any adjacent surfaces within an injector assembly. Also, separate seal assemblies may be connected to a common system 303, or separate systems 303, or combinations thereof.

Figure 8:
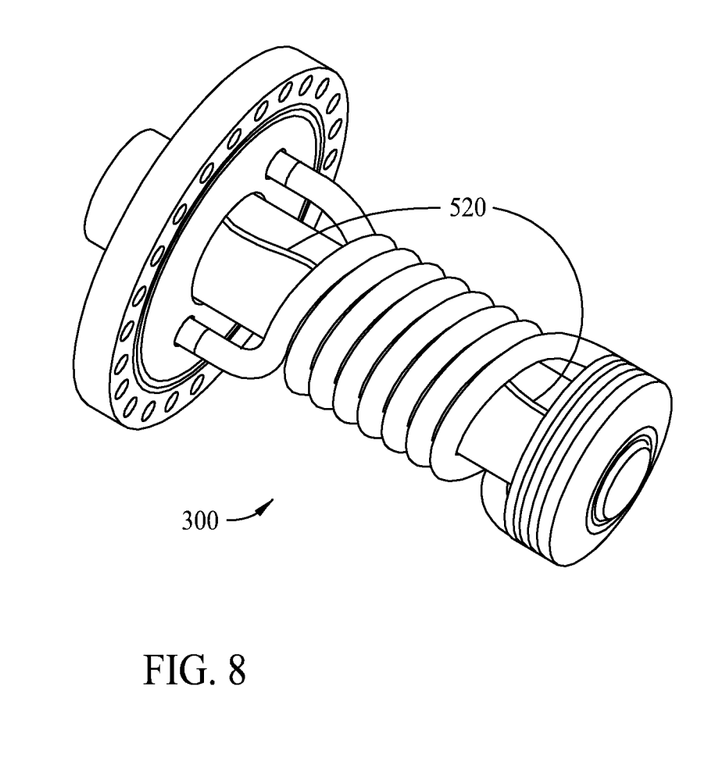
FIG. 8 is a perspective view of an exemplary injection device including buffer fluid supply tubing.

FIG. 8 is a perspective view of injection device 300 including seal buffer fluid supply tubing 520. The seal buffer fluid supply tubing 520 provides flow communication between seal pressure control and monitoring system 303 (shown in FIG. 2) and pressure port 414 (shown in FIG. 7). The seal buffer fluid supply tubing 520 is in flow communication with pressure port 414 and seal assembly 357. In other exemplary embodiments, seal buffer fluid supply tubing 520 may also be coupled in flow communication with other seal assemblies, including but not limited to, seal assemblies 358 and 359.

Figure 9:
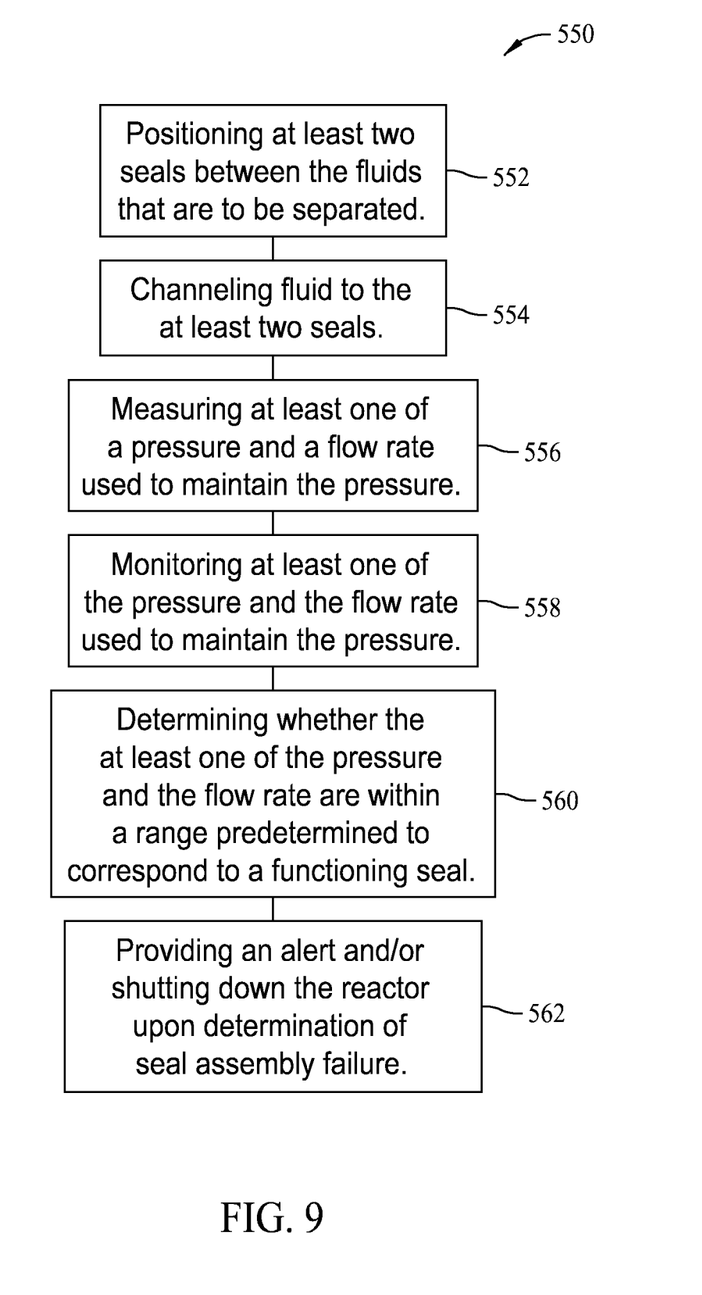
FIG. 9 is a block diagram of an exemplary method of monitoring seals in an injection device.

FIG. 9 is a block diagram of an exemplary method 550 for monitoring a functionality of a seal assembly, for example, seal assembly 357 (shown in FIG. 7) in an injection device, for example, injection device 300 (shown in FIG. 3). A functioning seal prevents fluid from leaking at a mating portion defined between, for example, outer GOX bayonet adapter 336 and outer GOX tip 500 (shown in FIG. 7). A certain amount of fluid may leak past a functioning seal, however, a seal becomes non-functioning, a condition referred to as a seal failure, when an amount of fluid leaking past the seal exceeds a predetermined level or amount as a result of, for example, seal wear, seal damage, and/or improper installation. An acceptable amount of fluid that may leak past a seal varies depending on the application of the seal.

Method 550 includes positioning 552 a seal assembly, for example, seal assembly 357, between the process fluids that are desired to be separated, and channeling 554 a fluid to seal assembly 357 to produce a fluid buffer. As described above, a variety of fluids may be used, including but not limited to, nitrogen and argon. Method 550 also includes measuring 556 a pressure of the buffer fluid provided to seal assembly 357, and/or a flow rate used to maintain the pressure. Method 550 further includes monitoring 558 the pressure and/or the flow rate used to maintain the pressure, and determining 560 whether measured pressure and/or flow rate are within a range predetermined to correspond to a functioning seal. If either the pressure or the flow rate are not within the predetermined range, in one example, a seal function alert is provided 562 to an operator of IGCC plant 100. In an exemplary embodiment, the seal function alert may be of varying levels to reflect the severity of the seal failure. In another embodiment, an automatic shutdown of gasification reactor 208 is performed if a seal failure is determined 560 to have occurred. Monitoring 558 may also include monitoring a composition of the buffer fluid and/or a process fluid. A changing composition of a fluid indicates that a fluid has leaked into, or out from, seal assembly 357.

The exemplary methods not only provide a method of monitoring the functionality of seals in an injection device, but also substantially prevent cross-leakage of the two process fluids being separated by the seals. Buffer fluid is injected into seal assembly 357 at a pressure that is higher than the pressure of the process fluids on opposing sides of seal assembly 357. Because the buffer fluid is at a pressure that is higher than the pressure of either of the two process fluids, should a seal failure occur, the buffer fluid would be the first fluid to leak. Additional damage may be prevented by channeling 554 a buffer fluid that will not react in a dangerous manner with either of the two process fluids. As described above, controlling which fluid initially leaks may prevent a potentially dangerous combination of fluids from undesirably mixing should a seal failure occur. A dangerous combination of fluids, such as GOX combined with syngas, may cause damage to injection device 300, gasification reactor 208, and/or other components within IGCC plant 100. However, if the non-reactive buffer fluid leaks out of the seal and the leak is detected, an orderly shutdown of the gasification reactor 208 may be performed before the leak becomes worse, and before any potentially dangerous fluids are mixed. The amount of time provided to perform the orderly shutdown while the higher pressure buffer fluid leaks out of the seal is at least partially dependent upon the severity of the leak, and the amount of buffer fluid that is available for injection into the seals.

Figure 10:
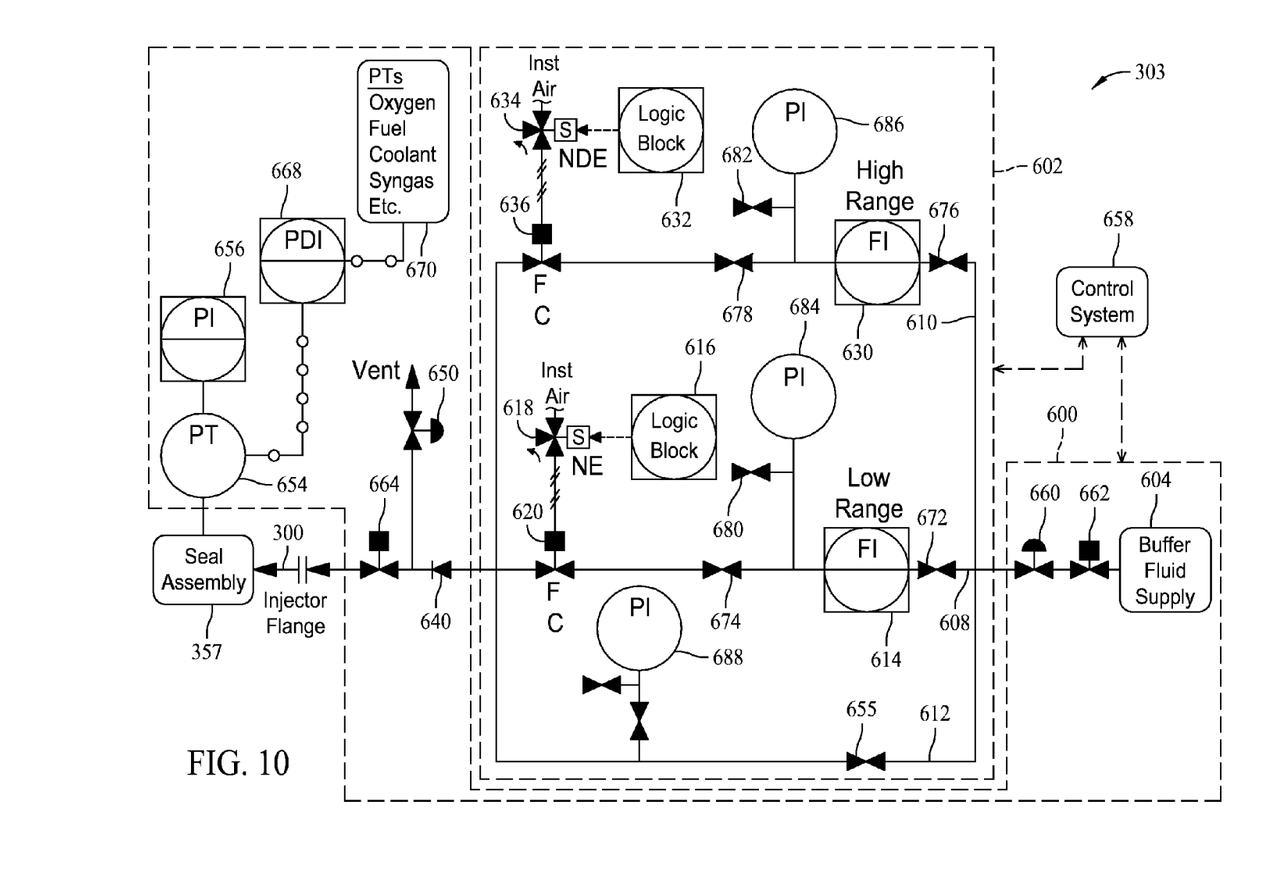
FIG. 10 is a piping and instrumentation diagram of an exemplary seal pressure control and monitoring system.

FIG. 10 is a simplified piping and instrumentation diagram of buffer fluid pressure control and monitoring system 303. In the exemplary embodiment, seal pressure control and monitoring system 303 controls fluid pressure in an injection device 300 seal assembly, for example, seal assembly 357 (shown in FIG. 7). For example, when seal assembly 357 is functioning properly, a small amount of buffer fluid may leak therethrough. Moreover, when seal assembly 357 is functioning properly, only the small amount of buffer fluid that is leaked has to be replaced in order to maintain a constant pressure at seal assembly 357. However, if seal assembly 357 is damaged or is not functioning properly, seal assembly 357 will generally leak a greater amount of buffer fluid. Accordingly, in order to attempt to maintain a substantially constant pressure at seal assembly 357, a higher rate of buffer fluid flow is required due to the greater amount of buffer fluid leaking from seal assembly 357. The health of a seal assembly can be determined by monitoring either the buffer seal fluid pressure and/or the buffer fluid rate of flow.

Buffer fluid pressure control and monitoring system 303 includes a buffer fluid supply system 600 and a buffer fluid monitoring system 602. Buffer fluid supply system 600 includes a buffer fluid source 604, a check valve 640, a pressure transmitter 654, a pressure indicator 656, a pressure control valve 660, and isolation valves 662 and 664. A control system 658 is coupled to buffer fluid supply system 600 and buffer fluid monitoring system 602. Control system 658 may alternatively be included within buffer fluid supply system 600 and/or buffer fluid monitoring system 602.

In the exemplary embodiment, a buffer fluid pressure in a seal assembly, for example, seal assembly 357, is detected by pressure transmitter 654. Pressure transmitter 654 converts the pressure into a pressure indication 656, which is provided to control system 658. Control system 658 regulates the flow of buffer fluid through control valve 660 based at least partially on pressure indication 656. In the exemplary embodiment, control valve 660 is positioned downstream from buffer fluid source 604 and upstream of buffer fluid monitoring system 602. For example, control system 658 sends a signal to increase the opening in control valve 660, thereby increasing a flow of buffer fluid to seal assembly 357, and increasing the pressure in seal assembly 357 when a pressure in seal assembly 357 falls below a set point value. Conversely, control system 658 sends a signal to decrease the opening in control valve 660 in order to decrease the flow of buffer fluid as a pressure in seal assembly 357 rises to approach the set point value. Alternatively, regulation of a pressure in seal assembly 357 may be facilitated instead using a pressure regulator or self-regulating pressure control valve (neither shown) located downstream of buffer fluid source 604 and upstream of buffer fluid monitoring system 602. Further alternatively, pressure in seal assembly 357 may be regulated via controls (not shown) included within buffer fluid source 604. Still further, the pressure in seal assembly 357 may be controlled by any means that facilitates operation of system 303 as described herein. In the exemplary embodiment, control system 658 is a distributed control system (DCS). Alternatively, control system 658 may be any suitable type of control system that facilitates the operation of system 303 as described herein.

In an alternative embodiment, control valve 650 is incorporated within system 303 as an automatic vent valve. Valve 650 is positioned downstream of buffer fluid monitoring system 602 and upstream of an isolation valve 664, and cooperates with pressure indicator 656, control system 658, and valve 660 to regulate a seal assembly 357 pressure by venting buffer fluid when a pressure in seal assembly 357 is higher than a desired set point. That is, control system 658 will cause valve 650 to open to avoid an excess pressure in seal assembly 357 or system 303, and then reclose when pressure indicator 656 is back to the desired level. Furthermore, in order to minimize the use of buffer fluid, a pressure set point or range of pressures that cause valve 650 to open is higher than a pressure set point or range of pressures that cause valve 660 to open, so that valves 650 and 660 are not open at the same time. Also, in some embodiments, a flow measuring device or system (neither shown) may be incorporated in system 303 to monitor a flow rate of buffer fluid vented through valve 650. Alternatively, valve 650 may be a pressure regulator or self-regulating pressure control valve. Further alternatively, pressure in seal assembly 357 may be regulated via controls included within buffer fluid source 604. Still further, the pressure in seal assembly 357 may be controlled by any means that facilitates operation of system 303 as described herein.

Buffer fluid pressure control and monitoring system 303 also includes buffer fluid monitoring system 602. In the exemplary embodiment, fluid monitoring system 602 includes three parallel flow rate metering branches: a low flow branch 608, a high flow branch 610, and a bypass branch 612. Low flow branch 608 includes a flow indicator 614 used to monitor a rate of fluid flow through branch 608, and a distributed control system (DCS) logic block 616 that is coupled in flow communication with a switch 618 and a valve 620. Switch 618 is normally energized, to force valve 620 into an open position.

High flow branch 610 includes a flow indicator 630 used to monitor a rate of fluid flow through branch 610. Flow indicators generally are able to measure a flow rate that is within a limited range. In an exemplary embodiment, flow indicator 630 is designed to measure higher flow rates than flow indicator 614, while having a lower end flow rate measuring capability overlapping the upper end flow rate measuring capability of flow indicator 614. In other words, the range of flow rates that flow indicator 630 is able to measure includes higher flow rates than the range of flow rates that flow indicator 614 is able to measure, but extends below the maximum flow rate that flow indicator 614 is able to measure. Conversely, flow indicator 614 is able to measure lower flow rates than the flow rates flow indicator 630 is able to measure, but extends to above the minimum flow rate that flow indicator 630 is able to measure. High flow branch 610 also includes a DCS logic block 632 coupled in flow communication with a switch 634 and a valve 636. Switch 634 is normally de-energized, to force valve 636 into a closed position.

Bypass branch 612 provides a bypass around low flow branch 608 and high flow branch 610. Bypass branch 612 includes a valve 655 that is closed unless low flow branch 608 and high flow branch 610 are being serviced. Bypass branch 612 allows buffer fluid to reach seal assembly 357 even when high flow branch 610 and low flow branch 608 are inoperative, for example, while instruments are being serviced.

When seal assembly 357 is functioning properly (i.e., no significant leakage), DCS logic block 632 controls switch 634 to close valve 636. Closing valve 636 closes high flow branch 610, preventing buffer fluid from flowing through high flow branch 610. Also, when seal assembly 357 is functioning properly, DCS logic block 616 controls switch 618 to open valve 620. Opening valve 620 allows the fluid from buffer source 604 to flow through low flow branch 608.

If seal assembly 357 is not functioning properly, and a significant leak forms, the flow rate of the fluid through low flow branch 608 will increase as buffer fluid source 604 continues to supply a buffer fluid at the same pressure as prior to the leak forming. DCS logic block 632 is configured to energize switch 634, opening valve 636, upon a rate of flow through flow indicator 614 reaching a predetermined percentage of the range of flow rates that flow indicator 630 is able to measure. Also, DCS logic block 616 is configured to de-energize switch 618, opening valve 620, when the rate of flow through flow indicator 614 is within a predetermined percentage of the range of flow rates that flow indicator 630 is able to measure. Opening valve 636 allows the buffer fluid to flow through high flow branch 610. As stated above, flow indicator 630 is able to measure higher flow rates than flow indicator 614.

Conversely, DCS logic block 632 is configured to energize switch 618, opening valve 620, when the rate of flow through flow indicator 630 reaches a predetermined percentage of the range of flow rates below which flow indicator 630 is unable to measure, allowing buffer fluid to flow through low flow branch 608. Also, DCS logic block 616 is configured to de-energize switch 634, closing valve 636. Closing valve 636 prevents buffer fluid from flowing through high flow branch 610.

In an exemplary embodiment, DCS logic blocks 616 and 632 may toggle valves 620 and 636. For example, upon receiving a signal from flow indicator 630 that the flow rate through flow indicator 630 has decreased to 10% of the maximum flow rate that flow indicator 630 is able to measure, or upon receiving a signal from flow indicator 614 that the flow rate through indicator 614 has reached 90% of the maximum flow rate that indicator 614 is able to measure, DCS logic blocks 616 and 632 toggle valves 620 and 636.

Flow indicators 614 and 630 are selected such that a range of flow rates through system 303 can be measured from a low flow rate when seal assembly 357 is functioning properly, to a high flow rate when seal assembly 357 is damaged and/or leaking.

System 303 also includes a check valve 640. Check valve 640 prevents backflow through system 303. For example, upon a seal failure, and also a buffer fluid supply failure that prevents system 303 from injecting seal assembly 357 with a buffer fluid, syngas from injection device 300 may reach seal assembly 357 and leak into system 303. Check valve 640 prevents the syngas from flowing toward buffer fluid source 604. Furthermore, isolation valves 662 and 664 may be automated to close, thereby isolating seal assembly 357, system 303, and buffer fluid source 604, in the event of such a leak or buffer fluid supply failure.

System 303 further includes isolation valves 672, 674, 676, and 678, vent valves 680 and 682, and local pressure indicators 684, 686, and 688 to facilitate the servicing of flow meters 614 and 630. More specifically, valves 672, 674 and 680, and pressure indicator 684, enable the isolation and depressurization of flow indicator 614, and of the lines between flow indicator 614, valves 676, 678, 682, and pressure indicator 686. Similarly, valves 672, 674 and 680, enable the isolation and depressurization of flow indicator 630, and of the lines between flow indicator 630, valves 676, 678 and 682, and pressure indicator 686. Also, local pressure indicator 688 facilitates servicing by providing a local pressure reading for system 303. Moreover, valves 672 and 676 may be used to bleed buffer fluid into and repressure flow indicators 614 and 630, respectively, reducing the potential of a temporary drop in the pressure of seal assembly 327 when putting flow indicators 614 and 630, respectively, back into service.

In an alternative embodiment, system 303 also includes a differential pressure indicator 668. Seal assembly 357 delta pressures are monitored by control system 658 to further monitor seal conditions and integrity. For example, a higher than normal buffer fluid flow rate at seal assembly 357 static pressure may be due to excessively high differential pressure across seal assembly 357 rather than an indication of seal integrity loss. On the other hand, a normal static pressure, combined with a normal buffer fluid flow rate, but a low differential pressure may be indicative of an excessive leak rate and reduced seal integrity.

Differential pressures between seal assembly 357 and the process fluids being separated by seal 357, or between seal assembly 357 and reactor 208 may be measured by differential pressure indicator 668. To ensure isolation of the process streams and the buffer fluid, differential pressure indicator 668 may use an output from pressure transmitters measuring the relevant pressures, such as pressure transmitter 654 and a pressure transmitter 670, rather than directly connecting a differential pressure transmitter to seal assembly 357 and a process stream or reactor 208. Pressure transmitter 670 may be coupled to, for example, but not limited to, an oxygen supply, a fuel supply, a coolant supply, and reactor 208. Alternatively, the differential pressure also may be determined within control system 658 by subtracting the values of the relevant static pressure indications.

In still another alternate embodiment, control system 658 may be used to regulate the flow rate of buffer fluid provided to seal assembly 357 to maintain at least one differential pressure across seal assembly 357 within a specific range of pressures. For example, seal life may be improved, and/or the use of lower cost seals may be enabled, by maintaining a pressure drop across the seal within a limited range of differential pressures, rather than allowing the differential pressure to vary significantly as a result of maintaining seal assembly 357 at a relatively constant high static pressure. That is, a differential pressure across seal assembly 357 may be maintained within a limited range of differential pressures, keeping seal loads low, while the static pressure within seal assembly 357 rises or falls as a function of adjacent process fluid or reactor 208 static pressures. Further alternatively, control system 658 may be used to monitor and regulate more than one pressure differential as well as the static pressure of seal assembly 357 within a set of predefined limits. Also, the set of predefined limits may either be a fixed set or a variable set, where the variable set takes into account the then current operating conditions within one or more of seal assembly 327, system 303, injector assembly 300, and/or reactor 208. For example, there may be one set of predefined limits used during startup and another set of predefined limits used during normal operation. Alternatively, there may be number of sets or predefined limits or programs used to regulate the pressure in seal assembly 357 that facilitate operation of system 303 as described herein.

The method and apparatus described herein, for monitoring the functionality of seals used in an injector assembly of a gasification system, facilitates the use of an injector assembly tip that includes both converging and diverging nozzles. An injector assembly tip portion having two sections, an adapter section and a modular tip section, facilitates service and maintenance of the injector assembly. Seal assemblies allow the adapter section and the modular tip section to be releasably coupled, while a separation between fluid channels is maintained. The converging and diverging nozzles allow syngas production fluid streams to be injected into the gasification reactor at predetermined orientations, which increases syngas production efficiency.

Furthermore, the method and apparatus described herein, for monitoring the functionality of seals, facilitates providing a seal failure alert upon the occurrence of a seal failure. The alert allows for an orderly system shutdown after a seal failure is detected. Also, use of a high pressure seal buffer fluid allows for control of which fluid is leaked in the event of a seal failure, which may prevent the mixture of potentially dangerous fluids.

Exemplary embodiments of syngas production as associated with IGCC plants are described above in detail. The methods, apparatus and systems are not limited to the specific embodiments described herein nor to the specific illustrated IGCC plants.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A seal monitoring system for monitoring functionality of at least one seal assembly in an injector feed assembly that includes a first section and a second section, the second section configured for coupling to the first section, wherein the first section and the second section each comprise at least one wall that defines at least one channel, said system comprising:

a buffer fluid supply system for supplying buffer fluid to a seal assembly positioned between the first section and the second section; and a buffer fluid monitoring system comprising at least one of a pressure monitor configured to monitor a pressure of the buffer fluid or a flow rate monitor configured to monitor a flow rate of the buffer fluid supplied to the seal assembly and to determine a functionality of the seal assembly based at least partially on at least one of the buffer fluid pressure or buffer fluid flow rate.

2. A seal monitoring system in accordance with claim 1 wherein said buffer fluid supply system supplies buffer fluid at a predefined pressure and flow rate.

3. A seal monitoring system in accordance with claim 2 wherein said buffer fluid supply system supplies buffer fluid to the seal assembly at a pressure that is greater than the pressures of either fluid separated by the seal assembly.

4. A seal monitoring system in accordance with claim 1 wherein said buffer fluid supply system further comprises a plurality of seal pressure branches configured to supply buffer fluid flow to the seal assembly.

5. A seal monitoring system in accordance with claim 4 wherein said buffer fluid monitoring system further comprises a plurality of flow rate monitors, each of said plurality of flow rate monitors coupled to one of said plurality of seal pressure branches and configured to measure a range of flow rates.

6. A seal monitoring system in accordance with claim 4 wherein at least two of said plurality of seal pressure branches comprise flow rate monitors configured to measure different flow rate ranges.

7. A seal monitoring system in accordance with claim 1 wherein said buffer fluid monitoring system determines a composition of at least one of the fluid and the buffer fluid and determines a functionality of the seal assembly based at least partially on the composition determination.

* * * * *